United States Patent
Kroos et al.

(10) Patent No.: US 10,139,222 B2
(45) Date of Patent: Nov. 27, 2018

(54) METHOD FOR THE ULTRASONIC MEASUREMENT OF A WALL THICKNESS IN HOLLOW VALVES

(71) Applicant: Mahle International GmbH, Stuttgart (DE)

(72) Inventors: Peter Kroos, Rutesheim (DE);
Christoph Luven, Stuttgart (DE);
Holger Schnell, Vaihingen/Enz (DE);
Thomas Strelow, Leutenbach (DE);
Richard Wlassa, Stuttgart (DE)

(73) Assignee: Mahle International GmbH (DE)

( * ) Notice: Subject to any disclaimer, the term of this patent is extended or adjusted under 35 U.S.C. 154(b) by 134 days.

(21) Appl. No.: 15/116,771

(22) PCT Filed: Nov. 20, 2014

(86) PCT No.: PCT/EP2014/075161
§ 371 (c)(1),
(2) Date: Aug. 4, 2016

(87) PCT Pub. No.: WO2015/117689
PCT Pub. Date: Aug. 13, 2015

(65) Prior Publication Data
US 2016/0349047 A1    Dec. 1, 2016

(30) Foreign Application Priority Data
Feb. 5, 2014 (DE) .................. 10 2014 202 021

(51) Int. Cl.
*G01N 29/07* (2006.01)
*F01L 3/20* (2006.01)
(Continued)

(52) U.S. Cl.
CPC ............ *G01B 17/02* (2013.01); *B23P 15/001* (2013.01); *F01L 3/14* (2013.01); *F16K 1/36* (2013.01);
(Continued)

(58) Field of Classification Search
CPC ...... G01N 29/04; G01N 29/07; G01N 29/221; G01N 29/245; G01N 29/262;
(Continued)

(56) References Cited

U.S. PATENT DOCUMENTS

| | | | |
|---|---|---|---|
| 3,382,707 A | 5/1968 | Heselwood | |
| 3,678,735 A | 7/1972 | Boulanger et al. | |

(Continued)

FOREIGN PATENT DOCUMENTS

| | | |
|---|---|---|
| DE | 2121412 A1 | 11/1971 |
| DE | 4019865 A1 | 1/1992 |

(Continued)

OTHER PUBLICATIONS

English abstract for DE-4019865.
(Continued)

*Primary Examiner* — Helen Kwok
(74) *Attorney, Agent, or Firm* — Fishman Stewart PLLC

(57) ABSTRACT

A method for measuring a wall thickness in hollow valves may include determining a wall thickness in a region of a valve stem using at least one ultrasonic sensor, wherein the one ultrasonic sensor may be oriented with respect to a surface on the valve stem in such a manner that an emitted ultrasound may be introduced into the surface in a perpendicular manner. The method may additionally or alternatively include determining a wall thickness in a region of a chamfer using the at least one ultrasonic sensor, wherein the at least one ultrasonic sensor may be positioned at a location on the chamfer at which an inner tangent in a cavity runs (Continued)

parallel to an outer tangent on the chamfer, and wherein the ultrasonic sensor is oriented with respect to the tangents in such a manner that an emitted ultrasound is introduced into the surface in a perpendicular manner.

20 Claims, 2 Drawing Sheets

(51) Int. Cl.
| | |
|---|---|
| *G01B 17/02* | (2006.01) |
| *B23F 15/00* | (2006.01) |
| *B23P 15/00* | (2006.01) |
| *F01L 3/14* | (2006.01) |
| *F16K 1/36* | (2006.01) |
| *G01N 29/04* | (2006.01) |
| *G01N 29/22* | (2006.01) |

(52) U.S. Cl.
CPC .............. *G01N 29/04* (2013.01); *G01N 29/07* (2013.01); *G01N 29/221* (2013.01); *F01L 2103/00* (2013.01); *G01N 2291/02854* (2013.01); *G01N 2291/101* (2013.01)

(58) Field of Classification Search
CPC .............. G01N 29/2437; G01N 29/343; G01N 29/4427; G01B 17/02; G01B 17/025; F16K 1/36; F16K 15/141; F16K 15/142; F01L 3/14; B23P 15/001
See application file for complete search history.

(56) References Cited

U.S. PATENT DOCUMENTS

| | | | | |
|---|---|---|---|---|
| 3,930,404 | A | | 1/1976 | Ryden, Jr. |
| 4,152,380 | A | | 5/1979 | Graves et al. |
| 4,437,332 | A | * | 3/1984 | Pittaro .................. G01B 17/02 73/1.82 |
| 4,520,672 | A | * | 6/1985 | Saint-Amour .......... B29C 47/92 264/40.1 |
| 4,597,294 | A | * | 7/1986 | Brill, III ............... F22B 37/003 376/252 |
| 4,715,008 | A | * | 12/1987 | Jones ..................... G01B 17/02 702/171 |
| 5,176,034 | A | * | 1/1993 | Hazony .................. G01B 17/02 73/597 |
| 5,549,004 | A | | 8/1996 | Nugent |
| 5,963,030 | A | * | 10/1999 | Stark ........................ G01B 7/12 324/228 |
| 7,600,530 | B2 | * | 10/2009 | Truitt .................... A61M 39/02 137/512 |
| 8,474,474 | B2 | * | 7/2013 | Wilke ................. F16K 37/0083 116/208 |
| 9,255,559 | B2 | * | 2/2016 | Kroos ................ F02M 63/0031 |
| 2002/0171846 | A1 | * | 11/2002 | Drake, Jr. ................ G01B 9/02 356/503 |
| 2003/0083576 | A1 | | 5/2003 | Bazarov et al. |
| 2011/0036439 | A1 | * | 2/2011 | Fernald .................. G01F 1/662 138/104 |
| 2017/0348782 | A1 | * | 12/2017 | Kroos ..................... B23H 9/14 |

FOREIGN PATENT DOCUMENTS

| | | |
|---|---|---|
| DE | 20207684 U1 | 8/2002 |
| DE | 102007011445 A1 | 9/2008 |
| EP | 0905478 A2 | 3/1999 |

OTHER PUBLICATIONS

English abstract for DE-102007011445.
English abstract for EP-0905478.
Sharma et al., "Non-Destructive Evaluation of Close Die Forged Main Body of Primary System Valves", Proceedings of the National Seminar & Exhibition on Non-Destructive Evaluation, NDE 2011, Dec. 8-10, 2011.

* cited by examiner

METHOD FOR THE ULTRASONIC MEASUREMENT OF A WALL THICKNESS IN HOLLOW VALVES

CROSS-REFERENCE TO RELATED APPLICATIONS

This application claims priority to German Patent Application No. 10 2014 202 021.2, filed Feb. 5, 2014, and International Patent Application No. PCT/EP2014/075161, filed Nov. 20, 2014, both of which are hereby incorporated by reference in their entirety.

TECHNICAL FIELD

The present invention relates to a method for measuring a wall thickness in hollow valves with and without a hollow valve head. The invention further relates to a method for producing a hollow valve with a hollow valve head.

BACKGROUND

Owing to their delicate embodiment, high quality requirements are often set for hollow valves, which must also be able to include samples up to a 100% testing. In particular, the maintaining of a predetermined wall thickness is an important quality factor in such hollow valves. In the simplest case in the case of a valve which is only bored hollow, this is the wall thickness in the stem and here, in particular, a possibly present centre offset of this bore, which has an effect on the wall thickness of the stem of the hollow valve. In this case, this can be established by measurement of the wall thickness on at least two or, better, four places or ideally even continuously on the circumference. In the case of constructed hollow valves made of sheet metal parts which are shaped and are welded to one another, the wall thickness measurement on the blank or respectively on the finished installed valve is likewise an essential quality feature, because through the shaping- and welding process deviations of the wall thickness can occur. In the case of hollow vales, on the other hand, in which a cavity is produced in the valve head by means of electrochemical machining (ECM), likewise the measurement of the wall thickness is extremely important, because electrochemical machining is poorly visible and hence poorly controllable and, moreover, is not defined by a solid cutter, such as for example in the production of a cavity with a drill. At the same time, in electrochemical machining a curved and irregular surface is produced, which in addition also forms an undercut. If a wall thickness can still be measured here tactilely in a relatively uncomplicated manner on the stem or respectively on the plate base, this is only possible with difficulty for the measurement of the wall thickness in the region of the chamfer. However, the measuring of the wall thickness in the region of the stem also already requires a comparatively long measurement time and a tactile approach. In addition, only the blank can be measured, because the finished produced valve generally does not enable any access for a tactile approach, as it has been filled with a cooling medium and closed. In order to save measuring time and in order to also be able to measure the wall thicknesses as simply as possible in the region of the chamfer, an ultrasonic measurement can be used, which, however, often presents difficulties in the case of curved surfaces and hence non-constant thicknesses or respectively oppositely-directed surfaces.

From DE 10 2007 011 445 B4 an ultrasonic method is known for the measurement of a wall thickness of a welded hollow beam, in which the hollow beam is closed at the ends in a pressure-tight manner by means of sealing elements and is acted upon by means of negative pressure or respectively positive pressure. Subsequently, a noise level is measured by an inspection unit, which is movable in the hollow beam, with an acoustic sensor directed substantially to the region of the weld seams, said noise level being produced by inflowing or outflowing air in the case of a crack in the weld seams of the hollow beam. To locate a crack which is detected by means of a flow noise, the respectively covered travelling distance of the acoustic sensor is determined by means of a path length measurement unit. This method is, however, able to be applied exclusively for comparatively large diameters of hollow sections.

From DE 202 07 684 U1 a device is known for ultrasonic thickness measurement within pipes, which is moved in the interior of a pipeline which is to be monitored and which has a housing with pieces of equipment contained therein for the measuring, processing and storing of measurement data. These pieces of equipment comprise an initiating pulse generator, an ultrasonic transmitter, an amplifier, a comparator with an analogue input, a digital clock timer, a processor and a digital data memory connected in series. This device is also, however, again moved in the interior of the pipeline which is to be measured, so that here, also, the cavity must have a certain diameter.

SUMMARY

The present invention is concerned with the problem of indicating a method for the measurement of a wall thickness in hollow valves with or without a hollow valve head, by means of which in particular also hollow valves produced by means of electrochemical machining having a hollow valve head can be tested in a precise manner with regard to their wall thickness.

This problem is solved according to the invention by the subject of the independent claims. Advantageous embodiments are the subject of the dependent claims.

The present invention is based on the general idea of arranging ultrasonic sensors at precisely selected and predefined locations of a hollow valve in a particular manner, and of obtaining via this an exact determining of the wall thicknesses. In the method according to the invention for the measurement of the wall thickness in hollow valves with and without a hollow valve head, a wall thickness is therefore determined in the region of a stem using at least one ultrasonic sensor, wherein in this case the ultrasonic sensor is oriented with respect to the surface on the stem in such a manner that the emitted ultrasound can be introduced into the surface in a perpendicular manner. Additionally or alternatively, a wall thickness in the region of a chamfer of the hollow valve with a hollow valve head is determined using likewise at least one ultrasonic sensor, wherein in this case the ultrasonic sensor is positioned at a location on the chamfer at which an inner tangent in the cavity of the valve head runs parallel to an outer tangent on the chamfer and wherein at the same time the ultrasonic sensor is oriented with respect to these two tangents in such a manner that the emitted ultrasound is introduced in a perpendicular manner to these tangents and in a perpendicular manner into the surface of the chamfer. With the method according to the invention, not only can also comparatively thin wall thicknesses of for example 0.8 to 3 mm be measured extremely precisely, but it is in particular also possible to detect exactly the wall thickness in a hollow valve with a cavity in the valve head produced by means of electrochemical machining and thereby to fulfil the comparatively high quality requirements in the region of the hollow valves. The location at which the ultrasonic sensor must be positioned in the region of the chamfer can already be established in advance by a design engineer, so that a corresponding testing device already applies the ultrasonic sensor in a defined manner at this location.

In an advantageous further development of the method according to the invention, the ultrasonic sensor is arranged at a range of $20°<\alpha<40°$ relative to a plate plane surface. In this angle range usually the location lies at which the tangents of both curved surfaces, i.e. the internal cavity surface and the external chamfer surface run parallel to one another. Through the exact definition of this location and selection of this angle range, a high repeat accuracy of the measurement or respectively testing is also possible.

Expediently, the measurement takes place in a fluid, in particular in oil, in an applied contact gel or in water provided with a corrosion protection. For the transmission of the sound waves, the ultrasonic sensor requires a suitable medium in order to be able to bridge the gap between sensor head and valve. This can be achieved for example with a contact gel. However, it is more expedient to submerge the complete hollow valve, at least in the region to be measured, into a fluid into which the ultrasonic sensor is also submerged. This is simple to arrange and is cost efficient, because the fluid can be used for a long time, whereas a contact gel must be washed off after use.

Generally, the surface quality of the hollow valve both externally in the region of the stem or respectively in the region of the chamfer should be as RZ25, in particular also less than RZ12, and moreover should have few grooves, which would falsify the wall thickness measurement.

In a further advantageous embodiment of the method according to the invention, the hollow valve which is to be measured is turned during the measurement or else two or four ultrasonic sensors are directed simultaneously onto the hollow valve which is to be measured. If only a single ultrasonic sensor is used, different measurement points can be approached by a simple turning of the hollow valve about its stem axis. In order to reduce the measurement time as a whole, of course also several ultrasonic sensors can be provided, distributed in the circumferential direction, which preferably carry out a wall thickness measurement simultaneously, whereby in particular also a turning of the hollow valve between two measurings can be dispensed with. Here, of course, it is immaterial in which position, for example with the valve base downward or upward, the measuring is carried out.

The present invention is based in addition on the general idea of indicating a method for the production of a hollow valve with a hollow valve head, in which by means of boring and/or electrochemical machining (ECM) a cavity is introduced into the hollow valve or respectively into the valve which is initially still configured as a solid valve. Immediately after the introducing of the cavity, a wall thickness of the hollow valve is then measured on the stem and/or on the chamfer by means of the previously described method. This offers the great advantage of already integrating the wall thickness measurement in an early manufacturing step, so that a hollow valve with insufficient wall thickness can already be rejected in good time, in particular before further expensive production steps (grinding/coating). Hereby, the manufacturing process as a whole can be configured so as to be more cost-efficient. In addition, owing to the constricted room, and the sole access possibility through a narrow stem bore, a tactile measuring is only possible by means of a special and extremely elaborate measuring device, which in addition would scarcely be suitable for a serial measurement owing to a long measurement duration. Furthermore, a tactile measuring is no longer possible in the case of a finished installed valve with filled cooling medium and with a closed valve stem.

Further important features and advantages of the invention will emerge from the subclaims, from the drawings and from the associated figure description with the aid of the drawings.

It shall be understood that the features mentioned above and to be explained further below are able to be used not only in the respectively indicated combination, but also in other combinations or in isolation, without departing from the scope of the present invention.

BRIEF DESCRIPTION OF THE DRAWINGS

Preferred example embodiments of the invention are illustrated in the drawings and are explained in further detail in the following description, wherein the same reference numbers refer to identical or similar or functionally identical components.

There are shown, respectively diagrammatically

DETAILED DESCRIPTION

Figure 1:
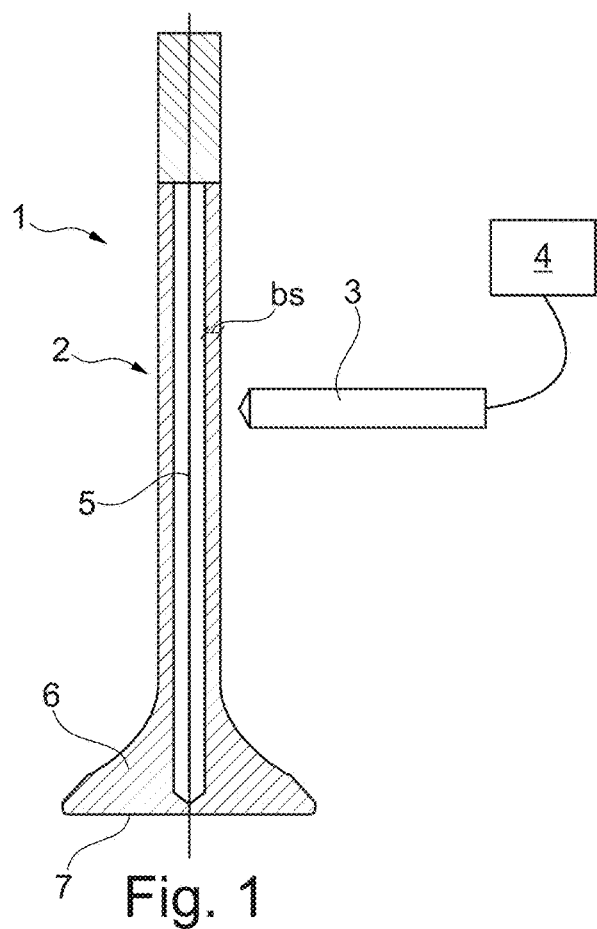
FIG. 1 a sectional illustration through a hollow valve during measurement of a wall thickness in the region of a valve stem, FIG. 2 a sectional illustration through a hollow valve in a cavity produced by means of electrochemical machining during the determining of wall thickness in the region of the cavity, FIG. 3 a device for carrying out the method according to the invention, FIG. 4 two diagrams for visualization of the wall thickness deviation, FIG. 5 the device according to the invention of FIG. 3 with a total of four ultrasonic sensors.

According to FIG. 1, a wall thickness $b_s$ of a hollow valve 1 is determined in the region of a valve stem 2 by means of at least one ultrasonic sensor 3, wherein the ultrasonic sensor 3 is oriented with respect to the surface on the valve stem 2 in such a manner that the emitted ultrasound is introduced into the surface in a perpendicular manner, here therefore perpendicularly to the axis of the hollow valve 1. The ultrasonic sensor 3 is configured here not only for emission, but also for reception of a reflected ultrasonic signal, which can then be evaluated by means of an evaluation unit 4. As can be seen from the illustration of FIG. 1, the hollow valve 1 has a drilled cavity 5, which extends not only over the valve stem 2 but into the region of the valve head 6.

Figure 2:
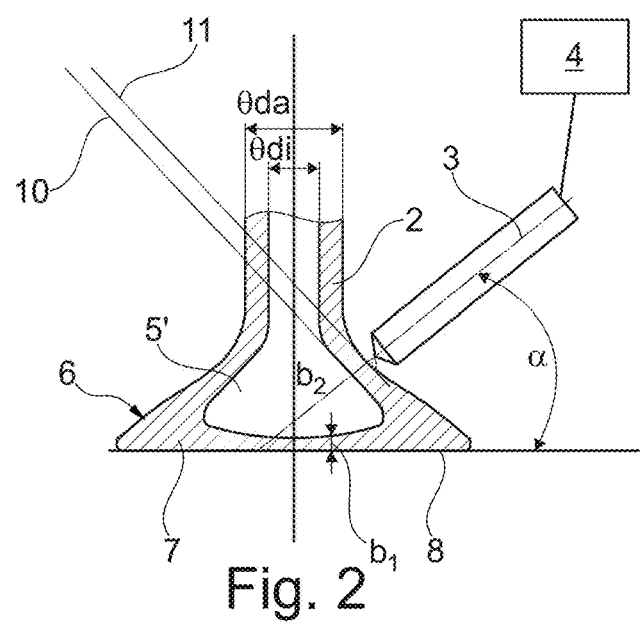

In contrast thereto, the hollow valve 1 illustrated according to FIG. 2 has in the region of its valve head 6 a cavity 5' produced by means of electrochemical machining (ECM), wherein the wall thickness $b_1$ or $b_2$ of a cavity 5' produced in such a manner, owing to the production process of the cavity 5' is distinctly more difficult to determine. The wall thickness $b_1$ lies here in the region of a valve base 7, which is defined by a plate plane surface 8. The wall thickness $b_2$, on the other hand, lies in the region of a chamfer 9. To determine the wall thickness $b_2$, the ultrasonic sensor 3 is now positioned at a location on the chamfer 9 at which an inner tangent 10 in the cavity 5' runs parallel to an outer tangent 11 on the chamfer 9 and wherein the ultrasonic sensor 3 is oriented with respect to these tangents 10, 11 in such a manner that the emitted ultrasound is introduced into the surface in a perpendicular manner and at the same time perpendicularly to the two tangents 10, 11 into the valve head 6 of the hollow valve 1. The perpendicular introducing of the ultrasound enables an exact determining of the wall thickness.

Observing FIG. 2 further, it can be seen that the ultrasonic sensor 3 is arranged in a range of 20°<α<40° relative to the plate plane surface 8, in this angle range normally the location lies at which the two tangents 10, 11 run parallel to one another.

Figure 3:
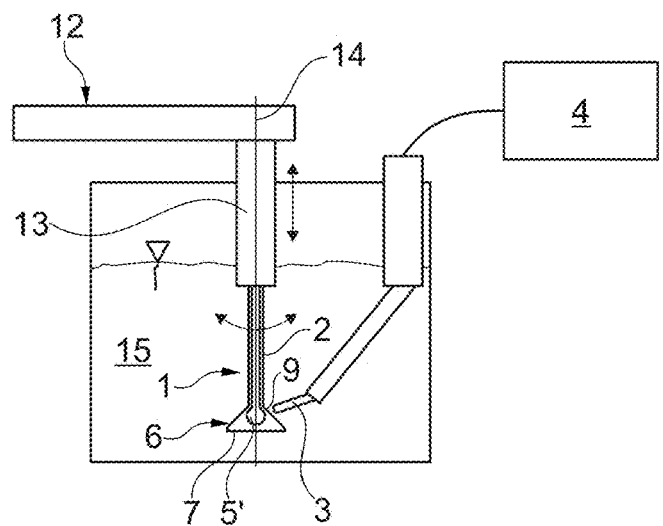

According to FIG. 3 a device 12 for carrying out the measurement method is shown, wherein the device 12 has an arm 13 holding the valve which is to be measured. This arm 13 is not only able here to turn the hollow valve 1, which is to be measured, about a valve axis 14, so that several measurement points or respectively several wall thicknesses $b_s$, $b_2$ can be determined in the region of the valve stem 2 or respectively of the chamfer 9, but it is in addition also able to submerge the hollow valve 1, which is to be measured, into a fluid 15, for example into oil or in water provided with a corrosion protection, so that the actual measuring of the wall thickness b takes place in the fluid 15. This is able to be accomplished in a considerably simpler, more cost-efficient and also better automatable manner than a measuring by means of contact gel, which firstly has to be applied and removed again after the measuring.

Figure 5:
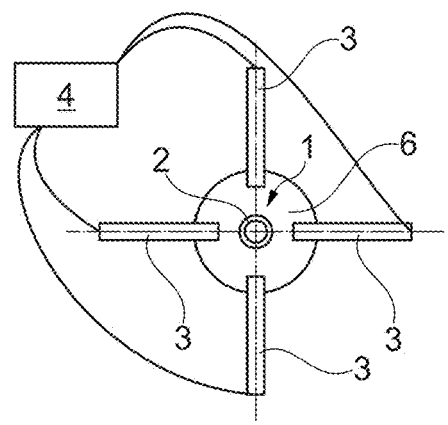

In order to be able to fulfil as high a quality standard as possible, the testing of the wall thickness $b_1$ or respectively $b_2$ or the wall thickness $b_s$ of the valve stem 2 should take place at several points, wherein there are basically two different method variants. According to the device 12 illustrated in FIG. 3, the hollow valve 1 which is to be measured is turned about its valve axis 14 during or respectively between two measurings. Alternatively hereto, it is also conceivable that two or, as is shown in FIG. 5, four ultrasonic sensors 3 are directed simultaneously onto the hollow valve 1 which is to be measured, whereby in particular also the cycle time for carrying out the wall thickness measurement can be reduced.

Figure 4:
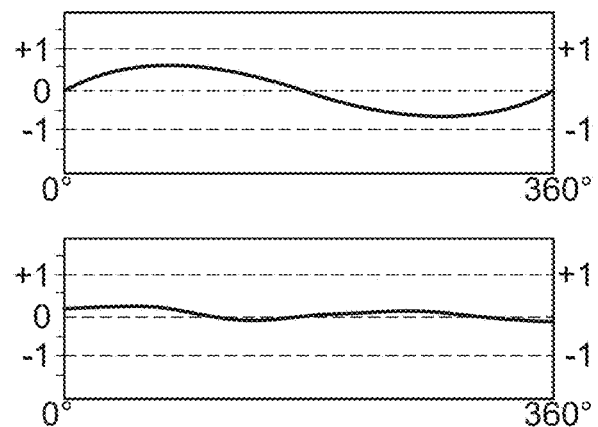

In FIG. 4 two diagrams are illustrated, which show a wall thickness deviation in the valve stem 2 in a reject part (upper illustration) and in a good part (lower illustration). It can be clearly seen here that the wall thickness deviation in the good part, illustrated below, runs closely around the zero line, whereas in the upper illustration in the reject part it is distributed comparatively widely. Such reject parts are therefore preferably already to be rejected in an early manufacturing step of the hollow valve 1, in particular directly after the production of the cavity 5, 5', and especially before further expensive and work-intensive manufacturing steps, such as for example a grinding or coating.

With the method according to the invention and with the device 12 according to the invention it is therefore possible to carry out a 100% testing of the produced hollow valves 1, whereby a high quality can be guaranteed.

The invention claimed is:

1. A method for measuring a wall thickness in hollow valves with and without a hollow valve head, comprising at least one of:
    determining a wall thickness in a region of a valve stem simultaneously using two or four ultrasonic sensors, wherein the ultrasonic sensors are oriented with respect to a surface on the valve stem in such a manner that an emitted ultrasound is introduced into the surface in a perpendicular manner; and
    determining a wall thickness in a region of a chamfer using at least one of the ultrasonic sensors, wherein the at least one of the ultrasonic sensors is positioned at a location on the chamfer at which an inner tangent in a cavity runs parallel to an outer tangent on the chamfer, and wherein the at least one of the ultrasonic sensors is oriented at an acute angle relative to a plate plane surface of a valve base, and oriented with respect to the tangents in such a manner that an emitted ultrasound is introduced into a surface of the chamfer in a perpendicular manner.

2. The method according to claim 1, wherein the acute angle is in a range between 20° and 40°.

3. The method according to claim 1, wherein the measuring takes place in a fluid.

4. The method according to claim 1, wherein the hollow valve to be measured is turned during the measuring.

5. The method according to claim 1, wherein at least one of the ultrasonic sensors is a high frequency ultrasonic sensor.

6. The method according to claim 1, wherein the wall thickness is measured in at least four circumferential locations of the hollow valve.

7. The method according to claim 1, wherein the wall thickness is measured on a blank or on a finished hollow valve, with a closed cavity.

8. The method according to claim 7, further comprising determining a wall thickness in a region of a valve base by at least one of the ultrasonic sensors, wherein the at least one of the ultrasonic sensors is oriented with respect to the plate plane surface of the valve base in such a manner that an emitted ultrasound is introduced into the plate plane surface in a perpendicular manner.

9. The method according to claim 1, wherein a relative movement takes place between the hollow valve to be measured and the ultrasonic sensors in a direction of an axis of the valve stem during the measuring.

10. A method for the production of a hollow valve with a hollow valve head, comprising:
    introducing a cavity into the hollow valve by at least one of boring and electrochemical machining (ECM); and
    measuring a wall thickness of the hollow valve on at least one of a valve stem, a chamfer, and a valve base by at least one of:
    determining the wall thickness in a region of the valve stem using two or four ultrasonic sensors, wherein the ultrasonic sensors are oriented with respect to a surface on the valve stem in such a manner that an emitted ultrasound is introduced into the surface in a perpendicular manner;
    determining the wall thickness in a region of the chamfer using at least one of the ultrasonic sensors, wherein the at least one of the ultrasonic sensors is positioned at a location on the chamfer at which an inner tangent in a cavity runs parallel to an outer tangent on the chamfer, and wherein the at least one of the ultrasonic sensors is oriented at an acute angle relative to a plate plane surface of the valve base, and is oriented with respect to the tangents in such a manner that an emitted ultrasound is introduced into a surface on the chamfer in a perpendicular manner; and
    determining the wall thickness in a region of the valve base at least one of the ultrasonic sensors, wherein the at least one of the ultrasonic sensors is oriented with respect to the plate plane surface of the valve base in such a manner that an emitted ultrasound is introduced into the plate plane surface in a perpendicular manner.

11. A hollow valve with or without a hollow valve head which was produced by;
  introducing a cavity into the hollow valve by at least one of boring and electrochemical machining (ECM); and
  measuring a wall thickness of the hollow valve on at least one of a valve stem, a chamfer, and a valve base by at least one of:
    determining the wall thickness in a region of the valve stem using two or four ultrasonic sensors, wherein the ultrasonic sensors are oriented with respect to a surface on the valve stem in such a manner that an emitted ultrasound is introduced into the surface in a perpendicular manner;
    determining the wall thickness in a region of the chamfer using at least one of the ultrasonic sensors, wherein the at least one ultrasonic sensors is positioned at a location on the chamfer at which an inner tangent in a cavity runs parallel to an outer tangent on the chamfer, and wherein the at least one of the ultrasonic sensors is oriented at an acute angle relative to a plate plane surface of the valve base, and is oriented with respect to the tangents in such a manner that an emitted ultrasound is introduced into a surface of the chamfer in a perpendicular manner; and
    determining the wall thickness in a region of the valve base using at least one of the ultrasonic sensors, wherein the at least one of the ultrasonic sensors is oriented with respect to the plate plane surface on the valve base in such a manner that an emitted ultrasound is introduced into the plate plane surface in a perpendicular manner.

12. The method according to claim 2, wherein the measuring takes place in a fluid.

13. The method according to claim 3, wherein the fluid is one of oil or water provided with a corrosion protection.

14. The method according to claim 2, wherein the hollow valve to be measured is turned during the measuring.

15. The method according to claim 2, wherein at least one of the ultrasonic sensors is a high frequency ultrasonic sensor is used.

16. The method according to claim 2, wherein the wall thickness is measured in at least four circumferential locations of the hollow valve.

17. The method according to claim 3, wherein the hollow valve to be measured is turned during the measuring.

18. The method according to claim 3, wherein at least one of the ultrasonic sensors is a high frequency ultrasonic sensor.

19. The method according to claim 3, wherein the wall thickness is measured in at least four circumferential locations of the hollow valve.

20. The method according to claim 3, wherein at least a portion of the hollow valve being measured is submerged in the fluid such that the measuring takes place in the fluid.

\* \* \* \* \*